United States Patent [19]
Inagi et al.

[11] Patent Number: 5,646,221
[45] Date of Patent: Jul. 8, 1997

[54] ADHESIVE BASE MATERIAL

[75] Inventors: Toshio Inagi, Mishima; Makoto Kanebako, Fuji, both of Japan

[73] Assignee: Kowa Co., Ltd., Nagoya, Japan

[21] Appl. No.: 622,288

[22] Filed: Mar. 25, 1996

[30] Foreign Application Priority Data

Mar. 31, 1995 [JP] Japan .................................. 7-075050

[51] Int. Cl.$^6$ .................................................. C08F 224/00
[52] U.S. Cl. .......................... 526/238.23; 526/238.2; 526/320; 526/321; 526/323.1; 526/323.2; 526/325; 527/300; 527/314
[58] Field of Search ................... 526/238.23, 238.2; 527/314, 300

[56] References Cited

U.S. PATENT DOCUMENTS

5,164,495  11/1992  Kitazawa ........................... 526/238.23
5,173,554  12/1992  Kitazawa ............................ 526/238.2

*Primary Examiner*—Fred Zitomer
*Attorney, Agent, or Firm*—Oblon, Spivak, McClelland, Maier & Neustadt, P.C.

[57] ABSTRACT

An adhesive base material comprises a polymer obtained by polymerizing a glucosyloxy alkyl (meth)acrylate, a hydroxyalkyl (meth)acrylate, an alkyl (meth)acrylate and a polyfunctional monomer. This adhesive base material can be caused to swell uniformly because of its good swelling property and exhibits excellent adhesion to the skin so that it is useful as adhesive layers in plasters, various medical pads and also medicament-impregnated dermatologic medicines.

12 Claims, 8 Drawing Sheets

ADHESIVE BASE MATERIAL

BACKGROUND OF THE INVENTION

1. Field of the Invention

This invention relates to an adhesive base material which contains a crosslinked polymer obtained by the polymerization of specific monomers, exhibits excellent adhesion to the skin, and is useful as plasters, medical pads, dermatologic medicines and the like.

2. Description of the Related Art

Known adhesive products for use in a form applied to the skin include those obtained by depositing a hydrophilic adhesive gel on a commercially-available support (Japanese Patents Laid-Open Nos. 111918/1987, 225314/1988, 246323/1988, etc.). Examples of support used in the above adhesive products include plastic sheets made of polyethylene, polypropylene, an ethylene-vinyl acetate copolymer, vinylon, a polyester, a polyurethane or nylon; nonwoven fabrics made of rayon or a polyester; and woven fabrics made of a polyester, an acrylic resin, silk or cotton. These supports are however accompanied with the problems that among them, the plastic sheets tend to peel off owing to the inferior adhesion with gel while the nonwoven and woven fabrics have poor flexibility and insufficient contraction.

As an adhesive base material to be impregnated with a water-soluble medicament, a water-soluble polymer or a water-soluble polymer having a crosslinked gel structure is used. Usable examples include polyacrylic acid, polyacrylate salts, polyvinyl alcohol, polyvinyl pyrrolidone, carboxymethylcellulose sodium, gelatin and starch. Among them, the polyacrylic acid and polyacrylate salts are used by converting them into gels crosslinked with a multi-valent metal salt prior to their impregnation with a medicament (Japanese Patent Laid-Open No. 15413/1978). The crosslinked gels so obtained are however accompanied with the problem that they occur as heterogeneous gels because of unduly rapid crosslinking reactions.

With a view to overcoming such problems, it has been attempted to use a sparingly water-soluble multi-valent metal salt to retard the reaction velocity (Japanese Patent Laid-Open No. 42617/1982). This attempt is however accompanied with the problems that it causes excessive retardation of the reaction, and that when the amount of the multivalent metal salt is increased to accelerate the reaction velocity, the swelling property of the gel is reduced, thereby deteriorating the absorption of the medicament.

It has therefore been attempted to add a metal sequestering agent such as ethylene diamine tetraacetic acid (EDTA), citric acid, lactic acid or the like to increase the crosslinking reaction velocity of a sparingly water-soluble multivalent metal salt (Japanese Patents Laid-Open Nos. 106598/1979, 11614/1984, 110617/1984, etc.). This attempt is however accompanied with the problems that because of insufficient sequestering of the multivalent metal ions, the crosslinking reaction velocity does not show a marked increase and moreover the swelling property of the gel is reduced by unsequestered multivalent metal ions.

Known adhesive products impregnated with a sparingly water-soluble medicament include those obtained by impregnating an acrylic adhesive with indomethacin and a chemical enhancer (Japanese Patent Publications Nos. 43368/1983 and 7688/1984). The medicament has such a small solubility in the adhesive that the adhesive base material cannot be impregnated with a clinically required amount of the medicament. With a view to overcoming that problem, it has been attempted to use a copolymer composed of a monomer having an intramolecular acid-amide bond and a (meth)acrylate ester (Japanese Patent Laid-Open No. 138426/1983); or to co-pulverize a water-soluble polymer and a sparingly water-soluble medicament, followed by mixing with a carboxyvinyl polymer, a basic substance and water (Japanese Patent Laid-Open No. 135924/1991). Such attempts are however not fully satisfactory from the viewpoint of controllability of the solubility of the medicament, the crosslinking reaction velocity, the swelling degree and the like.

SUMMARY OF THE INVENTION

An object of the present invention is therefore to provide an adhesive base material which has good swelling property, can be swelled uniformly and exhibits excellent adhesion to the skin.

Under the foregoing circumstances, the present inventors have carried out an extensive investigation. As a result, it has been found that an adhesive base material which exhibits excellent adhesion to the skin and has good swelling property can be obtained by using a polymer obtained by the polymerization of specific four monomers, leading to the completion of the present invention.

In one aspect of the present invention, there is provided an adhesive base material comprising a polymer obtained by polymerizing a glucosyloxy alkyl (meth)acrylate, a hydroxyalkyl (meth)acrylate, an alkyl (meth)acrylate and a polyfunctional monomer.

In another aspect of this invention, there is also provided a dermatologic medicine comprising the adhesive base material and a medicament.

The adhesive base material according to the present invention has good swelling property, can swell uniformly and exhibits excellent adhesion to the skin, so that it is useful as adhesive layers in plasters, various medical pads and medicament-impregnated dermatologic medicines. In particular, when formed into a dermatologic medicine impregnated with a medicament, the medicament shows excellent percutaneous absorption.

DETAILED DESCRIPTION OF THE PREFERRED EMBODIMENTS

The polymer suitable for use in the present invention is obtained by polymerizing (a) a glucosyloxy alkyl (meth)

acrylate, (b) a hydroxyalkyl (meth)acrylate, (c) an alkyl (meth)acrylate and (d) a polyfunctional monomer.

Examples of the glucosyloxy alkyl (meth)acrylate (a) usable herein include those represented by the following formula (1):

wherein R represents a hydrogen atom or a methyl group, G—O— represents a saccharide residual group having no protecting group, and n stands for 2 or 3.

Preferred examples of the saccharide residual group represented by G—O— in the formula (1) include those having 1 to 10, especially 1 to 5 saccharide units and derived from monosaccharides and oligosaccharides, respectively. Specific examples of the monosaccharides include hexoses such as glucose, mannose, galactose, glucosamine, mannosamine and galactosamine; and pentoses such as arabinose, xylose and ribose. Specific examples of the oligosaccharides, on the other hand, include disaccharides such as maltose, lactose, trehalose, cellobiose, isomaltose, gentiobiose, melibiose, laminaribiose, chitobiose, xylobiose, mannobiose and sophorose; maltotriose; isomaltotriose; maltotetraose; maltopentose; mannotriose; manninotriose; and hydrolyzates of starch, cellulose, chitin, chitosan and mannan, such as dextrin listed in the Pharmacopoeia of Japan, achrodextrin, British gum and cellodextrin.

In the formula (1), a methyl group and 2 are preferred as R and n, respectively.

Particularly preferred examples of the monomer (a) include 2-glucosyloxyethyl methacrylate, 2-mannosyl-oxy ethyl methacrylate and 2-galactosyloxyethyl methacrylate.

Examples of the hydroxyalkyl (meth)acrylate (b) include 2-hydroxyethyl (meth)acrylate and hydroxypropyl (meth)acrylate. Of these, 2-hydroxyethyl methacrylate is particularly preferred from the viewpoints of the safety to the body and the like.

Illustrative of the alkyl (meth)acrylate (c) include ethyl (meth)acrylate, n-butyl (meth)acrylate, isobutyl (meth)acrylate, hexyl (meth)acrylate, octyl (meth)acrylate, 2-ethylhexyl (meth)acrylate, isooctyl (meth)acrylate, decyl (meth)acrylate, isodecyl (meth)acrylate, lauryl (meth)acrylate and stearyl (meth)acrylate. Of these, particularly preferred are n-butyl acrylate and 2-ethylhexyl acrylate which have been used widely as an adhesive layer component in cataplasms.

It is preferred to mix the glucosyloxy alkyl (meth)acrylate (a), the hydroxyalkyl (meth)acrylate (b) and the alkyl (meth) acrylate at a molar ratio of 0.1–10:10–40:5–20, more preferably 0.1–10:19:10 and still more preferably 0.1–2:19:10.

As the polyfunctional monomer (d), any monomer can be used insofar as it has at least two functional groups per molecule. Examples include monomers having at least two vinyl groups per molecule such as ethylene glycol di(meth) acrylate, diethylene glycol di(meth)acrylate, triethylene glycol di(meth)acrylate, polyethylene glycol di(meth)acrylate, propylene glycol di(meth)acrylate, polypropylene glycol di(meth)acrylate, 1,4-butylene glycol di(meth)acrylate, 1,6-hexanediol di(meth)acrylate and 1,10-decanediol di(meth) acrylate; monomers having at least two allyl groups per molecule such as diallyl phthalate, diallyl maleate, diallyl adipate, triallyl isocyanate and diethylene glycol bisallylcarbonate; and N,N'-methylenebisacrylamide. Of these, preferred are ethylene glycol dimethacrylate (EGDMA) and triethylene glycol dimethacrylate (TEGDMA) for their particularly high safety.

The preferred molar ratio of the polyfunctional monomer (d) to the sum of the glucosyloxy alkyl (meth)acrylate (a), hydroxyalkyl (meth)acrylate (b) and alkyl (meth)acrylate (c) falls within a range of from 1:100 to 1:3200, with a range of from 1:200 to 1:800 being particularly preferred. The smaller the molar ratio of the polyfunctional monomer, the higher the swelling rate but the lower the mechanical strength. A molar ratio within the above range is therefore preferred.

The polymer suitable for use in the present invention can also be obtained by additionally polymerizing one or more monomers other than the above monomers (a) through (d). Illustrative of such additional monomers include carboxyl-containing, amido-containing and amino-containing monomers. Examples of the carboxyl-containing monomers include unsaturated carboxylic acids such as (meth)acrylic acid, maleic acid, fumaric acid and crotonic acid; examples of amido-containing monomers include (meth)acrylamide, dimethyl(meth)acrylamide, diethyl (meth)acrylamide, butoxymethyl(meth)acrylamide, ethoxyethyl (meth) acrylamide, diacetone (meth)acrylamide and vinylpyrrolidone; and examples of amino-containing monomers include dimethylamino(meth)acrylate and diethylamino(meth) acrylate. Further examples include vinyl acetate, styrene, vinyl chloride, acrylonitrile, ethylene, propylene and butadiene.

No particular limitation is imposed on the polymerization process. The polymerization of the glucosyloxy alkyl (meth) acrylate (a), hydroxyalkyl (meth)acrylate (b), alkyl (meth) acrylate (c) and polyfunctional monomer (d) may therefore be conducted in a manner known per se in the art.

No particular limitation is imposed on a polymerization initiator suitable for use in the radical polymerization. A suitable polymerization initiator can be selected depending on the monomers, a reaction solvent and the like. When a water-soluble monomer or, as a reaction solvent, a water-containing solvent is employed, usable examples of the polymerization initiator include persulfates such as ammonium persulfate and potassium persulfate. When a hydrophobic monomer or, as a reaction solvent, an organic solvent is employed, usable examples of the polymerization initiator include peroxides such as benzoyl peroxide, di-tert-butyl peroxide and acetyl peroxide; and azo compounds such as 2,2'-azobisisobutylonitrile, 2,2'-azobis(2-methylbutylonitrile), 2,2'-azobis(2,4-dimethylvaleronitrile) and dimethyl-2,2'-azobis(2-methylpropionate).

It is desired to add the polymerization initiator in an amount of 0.01 to 10 wt. % based on the sum of the monomers.

Examples of the solvent suitable for use in conducting the polymerization by solution polymerization include water, methanol, isopropyl alcohol, dioxane, tetrahydrofuran, acetone, acetonitrile, dimethyl formamide and dimethyl sulfoxide. These solvents can be used either singly or in combination.

When a conventional radical polymerization initiator is used, for example, it is preferred to conduct the polymerization reaction at 25° to 100° C. for 2 to 72 hours. To increase the polymerization degree by decomposing the polymerization initiator, it is preferred to conduct the polymerization reaction for a predetermined time and then to proceed further with the polymerization reaction at an elevated temperature.

Alternatively, it is also possible to conduct the polymerization without using any polymerization initiator. This can be effected by exposing the monomers to radiation, light, ultraviolet rays or low-temperature plasma to form polymerization-initiating free radicals and then performing the polymerization. Examples of the radiation usable here include high-energy ionizing radiation such as α-rays, β-rays, γ-rays, accelerated electrons and X-rays. Of these, γ-rays and accelerated electrons are preferred. Exposure to light or ultraviolet rays can generally be conducted using a mercury lamp, with the exposure through a filter at a wavelength of at least 300 nm being preferred. Preferred examples of the low-temperature plasma include those obtained by a glow discharge or a corona discharge. It is desired to add an oxygen scavenger upon such polymerization.

Exclusion of the polymerization initiator makes it possible to avoid the toxicity of the polymerization initiator. After the polymerization reaction, the resultant polymer can be purified in a manner known per se in the art.

Of polymers available by conducting polymerization reactions as described above, the polymer obtained by polymerizing 2-glucosyloxyethyl (meth)acrylate, 2-hydroxyethyl (meth)acrylate, n-butyl (meth)acrylate and ethyleneglycol di(meth)acrylate is particularly preferred.

The polymer so obtained can be caused to swell by impregnating it with a solvent or by doing so after pulverization. Examples of the solvent usable for this purpose include water; polyhydric alcohols such as ethylene glycol, propylene glycol, diethylene glycol, glycerin, polyethylene glycol, triethylene glycol, ethylene glycol monoethyl ether, ethylene glycol monobutyl ether, diethylene glycol monomethyl ether, polypropylene glycol, batyl alcohol, pentaerythritol and sorbitol; and monohydric alcohol such as ethanol, isopropyl alcohol, lauryl alcohol, cetyl alcohol, stearyl alcohol, oleyl alcohol and lanolin alcohol. It is desired to use them either singly or in combination. Of these, a mixed solvent of an alcohol and water is preferred, and a mixed solvent of a polyhydric alcohol, a monohydric alcohol and water is particularly preferred, with that of polyethylene glycol as a polyhydric alcohol, isopropyl alcohol as a monohydric alcohol, and water being more preferred. When used as a mixed solvent, it is desired to use a polyhydric alcohol, a monohydric alcohol and water at a weight ratio of 0.5–5:0.1–2:1.

The adhesion of the polymer can be enhanced when used in a pulverized form, although it can also be used as is or in the form of a plate. The pulverization makes it possible to impregnate the polymer uniformly with the solvent and further, to enlarge the surface area of the polymer per unit weight, thereby increasing its swelling speed and swelling degree. The swelling time of a gel is known to be proportionate to the square of the length of the gel. It is therefore desired to reduce the particle size of the gel as small as possible to increase the swelling degree in a short time. In the present invention, the preferred particle size of the pulverized polymer falls within a range of from 200 to 50 mesh.

The plate polymer can be formed into an adhesive base material by causing it to swell in a mixed solvent of an alcohol and water and then cutting the resulting polymer into a piece of desired area. The pulverized polymer can be formed into an adhesive base material by blending it with a mixed solvent of an alcohol and water at a weight ratio of 1:1 to 1:10, preferably 1:3 to 1:7 and then spreading the resulting mixture to a desired area between sheets of a tack-free resin or rubber such as silicone or TEFLON with a spacer of a desired thickness interposed therebetween.

In the present invention, the polymer having a swelling rate of 300% or greater when impregnated with a solvent is preferred because it has enhanced adhesion to the skin at such a swelling rate. To heighten the swelling rate, it is only necessary to lower the crosslink density or to use a crosslinking agent of a longer chain length. The crosslink density or the chain length of the crosslinking agent can be selected as desired to an extent not impairing the mechanical strength of the polymer. In addition, it is desired to determine the swelling rate at need according to the application or the like of the adhesive base material of the present invention.

Incidentally, the swelling rate can be determined by the following formula:

$$\text{Swelling rate (\%)} = \frac{W - W_o}{W_o} \times 100 \qquad (1)$$

$W_o$ = Initial weight
$W$ = Weight upon saturated swelling

The polymer swelled by the impregnation with a solvent preferably has peel strength of 80 g/cm² or greater when measured relative to glass. Peel strength of 100 g/cm² or greater is particularly preferred because excellent adhesion to the skin can be obtained.

The peel strength can be determined by the following formula:

$$\text{Peel strength (g/cm}^2\text{)} = \frac{W_D}{A} \qquad (2)$$

$W_D$: Load upon peeling
$A$: Cross section area of sample

The adhesive base material according to the present invention can also be used in a form deposited on a commercially-available support. Illustrative usable examples include plastic sheets made of polyethylene, polypropylene, an ethylene-vinyl acetate copolymer, vinylon, a polyester, polyurethane, nylon or the like; nonwoven fabrics made of rayon, a polyester or the like; and woven fabrics made of a polyester, an acrylic resin, silk, cotton or the like.

For use as a dermatologic medicine, the adhesive base material can be prepared by dissolving an appropriate medicament in a solvent and then impregnating the polymer with the resulting solution. The adhesive base material so obtained features good percutaneous absorption of the medicament. No particular limitation is imposed on the medicament insofar as it can be absorbed percutaneously. Examples include antipyretic, antiphlogistic and analgesic agents, steroidal anti-inflammatory agents, vasodilators, antihypertensive and antiarrhythmic agents, hypotensive agents, antitussive expectorants, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics and antibiotics.

Specific examples of the antipyretic, antiphlogistic and analgesic agents include indomethacin, salicylic acid, aspirin, acetaminophen, sodium dichlofenac, ibuprofen, sulindac, naproxen, ketoprofen, flufenamic acid, ibufenac, fenbufen, alclofenac, phenylbutazone, mefenamic acid, bendazac, piroxicam, flurbiprofen, pentazocine, buprenorphine hydrochloride and butorphanol tartrate.

Examples of the steroidal anti-inflammatory agents include hydrocortisone, prednisolone, fluocinolone acetonide, fludroxycortide, methyl prednisolone, hydrocortisone acetate, triamcinolone acetonide, dexamethasone, betamethasone acetate, diflucortolone velerate, clobetasol propionate and fluocinonide.

Examples of the vasodilators include diltiazem, verapamil, pentaerythritol tetra-acetate, dipyridamole, isosorbide nitrate and nifedipine.

Examples of the antihypertensive and antiarrhythmic agents include propranolol, atenolol, pindolol, kinidine sulfate, ajimaline, alprenolol hydrochloride, metoprolol tartrate, nadolol, timolol maleate and disopyramide.

Examples of the hypotensive agent include clonidine hydrochloride, captopril, prazosin hydrochloride, penbutolol sulphate, guanabenz acetate, guanfacine hydrochloride, bunazosin hydrochloride, enalapril maleate, alotinolol hydrochloride and bunitrolol hydrochloride.

Examples of the antitussive expectorants include procaterol hydrochloride, terbutaline sulfate, fenoterol hydrobromide, tulobuterol hydrochloride, ambroxol hydrochloride, pirbuterol hydrochloride, mabuterol hydrochloride, clenbuterol hydrochloride, trimetoquinol hydrochloride and formoterol fumarate.

Illustrative of the antineoplastics include glycolpyrronium bromide.

Examples of the local anesthetics include benzocaine, procaine, lidocaine and tetracaine.

Examples of the hormone preparations include steroidal hormone preparations such as estrogen, estradiol, testosterone, progesterone and prostaglandin; and peptide hormone preparations such as insulin.

Examples of the antiasthmatic and antiallergic agents include ketotifen fumarate, azelastine hydrochloride and sodium cromoglycate.

Examples of the antihistaminics include cycloheptadine hydrochloride, diphenhydramine hydrochloride, phenbenzamine and mequitazine.

Examples of the anticoagulants include heparin, urokinase and tPA and those of antispasmodics include scopolamine and clofluperrole.

Examples of the cerebral circulation and metabolism improvers include vinpocetine, flunarizine hydrochloride, nicardipine hydrochloride, brovincamine fumarate, dihydroergotoxine mesylate, ifenprodil tartrate and isoxsuprine hydrochloride.

Examples of antidepressant and antianxiety agents include maprotiline hydrochloride, etizolam, diazepam, bromazepam, amitriptyline hydrochloride and mianserin hydrochloride.

Examples of the vitamin D preparations include alfacalcidol and ergocalciferol.

Examples of the hypoglycemic agents include glibenclamide and gliclazide.

Examples of the antiulcer agents include clebopride malate, famotidine and glycopyrronium bromide.

Examples of the hypnotics include phenobarbital and amobarbital.

Examples of the antibiotics include tetracycline and chloramphenicol.

Although the amount of the medicament to be dissolved in a solvent differs with its clinically-required amount and a single dosage, preferred is 0.1 to 10 wt. % to the mixed solvent of an alcohol and water. It is also possible to add at need one or more ingredients usually employed for a dermatologic medicine, such as a skin irritant, chemical enhancer, stabilizer, aging resistant, sunscreening agent and/ or antioxidant. In addition, the pH of the dermatologic medicine can be adjusted with an acid or alkali.

The adhesive base material containing a medicament therein can be used as pads for iontophoresis or phonophoresis as well as usual plasters.

EXAMPLES

The present invention will hereinafter be described more specifically by the following examples. It should however be borne in mind that this invention is by no means limited to or by the examples.

EXAMPLE 1

2-glucosyloxyethyl methacrylate (hereinafter abbreviated as "GEMA"), 2-hydroxyethyl methacrylate (hereinafter abbreviated as "HEMA") and n-butyl acrylate (hereinafter abbreviated as "BA") were mixed at varied molar ratios of 0.1–10:19:10, whereby various monomer mixtures were obtained. To each of the resulting monomer mixtures, ethyleneglycol dimethacrylate (hereinafter abbreviated as "EGDMA") was added at a molar ratio of 800 to 1, followed by the further addition of 2,2'-azobisisobutylonitrile in an amount of 0.1 wt. % based on the entirety of the resulting monomer mixture. After nitrogen purging and deaeration, the resulting mixture was subjected to polymerization reaction at 65° C. for 5 hours and further at 75° C. for one hour.

After the completion of the polymerization reaction, a series of procedures, that is, swelling with isopropyl alcohol, washing with water, vacuum drying and pulverization, was repeated twice to purify the resulting polymer. The polymer so purified was pulverized in a pulverizer, followed by sifting through an 80-mesh sieve, whereby the polymer was obtained in the form of fine powder.

The resulting fine powdery polymer and a 2:1:1 mixed solution of polyethylene glycol, isopropyl alcohol and water were combined at a weight ratio of 1 to 5. 0.4 g of the resulting mixture was weighed and then caused to spread to an area of 2 cm×2 cm between two silicone sheets with a 0.5 mm-thick spacer interposed therebetween, whereby a pad was produced. In this manner, various pads were produced.

EXAMPLE 2

Between two slide glasses with a 0.5 mm-thick spacer interposed therebetween, polymerization reaction was conducted as in Example 1.

After the completion of the polymerization reaction, a series of the procedures, that is, swelling with isopropyl alcohol, washing with water and drying, was repeated twice to conduct purification. In this manner, various polymers were obtained each in the form of a plate.

EXAMPLE 3

To a 1:19:10 (molar ratio) monomer mixture of GEMA, HEMA and BA, EGDMA was added at varied molar ratios of from 100:1 to 1600:1. The resulting mixtures were treated in a similar manner to Example 1, whereby various polymers were obtained each in a fine powdery form. Pads were produced from the resulting fine powdery polymers, respectively.

EXAMPLE 4

As in Example 3, polymerization was conducted between two slide glasses with a 0.5 mm-thick spacer interposed therebetween. After the completion of the polymerization, the resulting polymer was purified as in Example 2. In this manner, various polymers were obtained each in the form of a plate.

EXAMPLE 5

To a 1:19:10 (molar ratio) monomer mixture of GEMA, HEMA and BA, EGDMA or triethyleneglycol dimethacrylate (TEGDMA) was added at a molar ratio of 800 to 1. The resulting mixture was treated in a similar manner to Example 1. In this manner two polymers were obtained each in a fine powdery form. Pads were then produced from the fine powdery polymers, respectively.

EXAMPLE 6

As in Example 5, polymerization was conducted between two slide glasses with a 0.5 mm-thick spacer interposed therebetween. After the completion of the polymerization, the resulting polymer was purified as in Example 2. In this manner, two polymers were obtained each in the form of a plate.

TEST 1

Of the polymers obtained in Examples 1 through 6, the plate-shaped polymers were each cut into pieces of 1 cm×1 cm, followed by vacuum drying. The pieces of each plate polymers were impregnated with a mixed solvent of 1 part by weight of indomethacin, 49 parts by weight of PEG 400, 25 parts by weight of isopropyl alcohol and 25 parts by weight of water to cause swelling. On the other hand, fine powdery polymers which had been obtained by pulverizing the plate-shaped polymers in a pulverizer and then sifting the thus-pulverized polymers through a 80-mesh sieve, respectively, and one part by weight of the fine powdery polymers obtained in the above examples were individually mixed with 5 parts by weight of a mixed solvent of the same composition as the above one, followed by spreading and swelling.

As a result of visual observation on the forms of the polymers after the swelling, it was found that each polymer was impregnated uniformly with the solvent. It was also found that compared with the plate-shaped polymers, the fine powdery polymers were impregnated more uniformly.

TEST 2

The plate polymers obtained in the above examples were each cut into pieces of 1 cm×1 cm, followed by vacuum drying. The pieces of the plate polymers so obtained were then impregnated with PEG400 or with an aqueous solution of PEG 400. The weights of the resulting samples upon saturated swelling were measured about one week after the impregnation and then swelling rates were calculated in accordance with the above-described formula (1).

Figure 1:
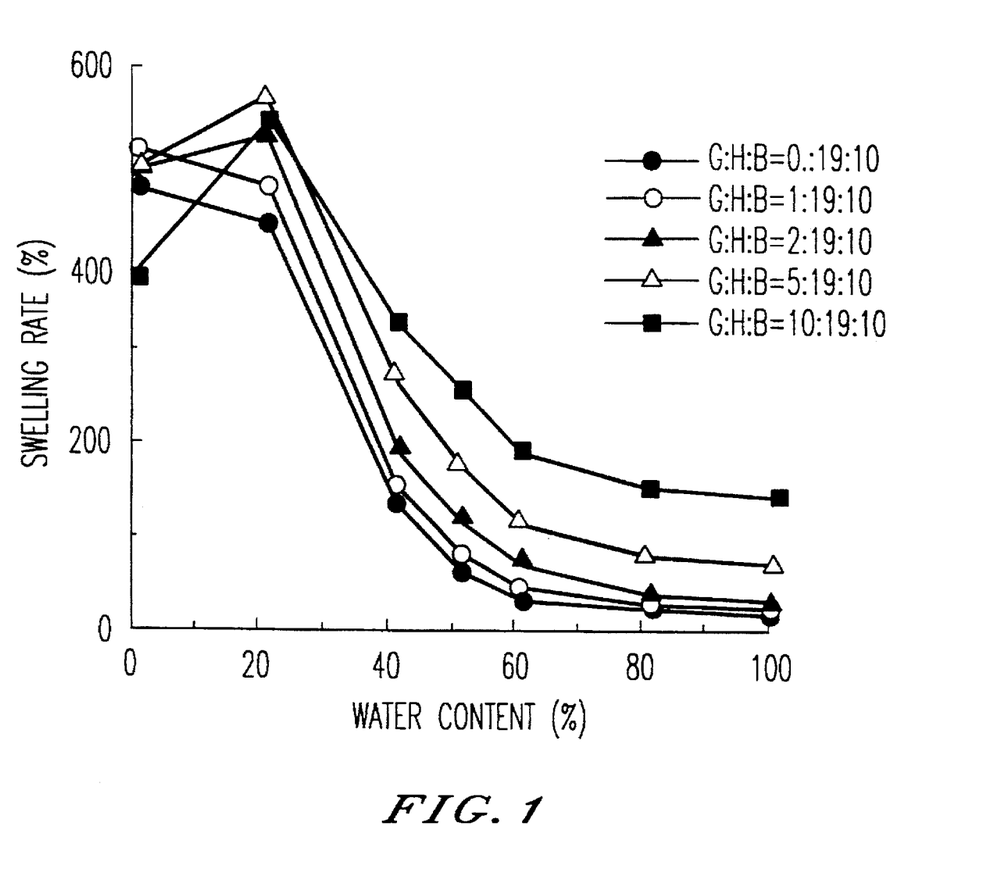
FIG. 1 diagrammatically illustrates a comparison in swelling rate among polymers with varied proportions of GEMA.

FIG. 1 shows a comparison in swelling rate among the plate-shaped polymers obtained in Example 2 at the varied mixing ratios of GEMA.

The maximum swelling rate was observed at the water content of 20%.

Figure 2:
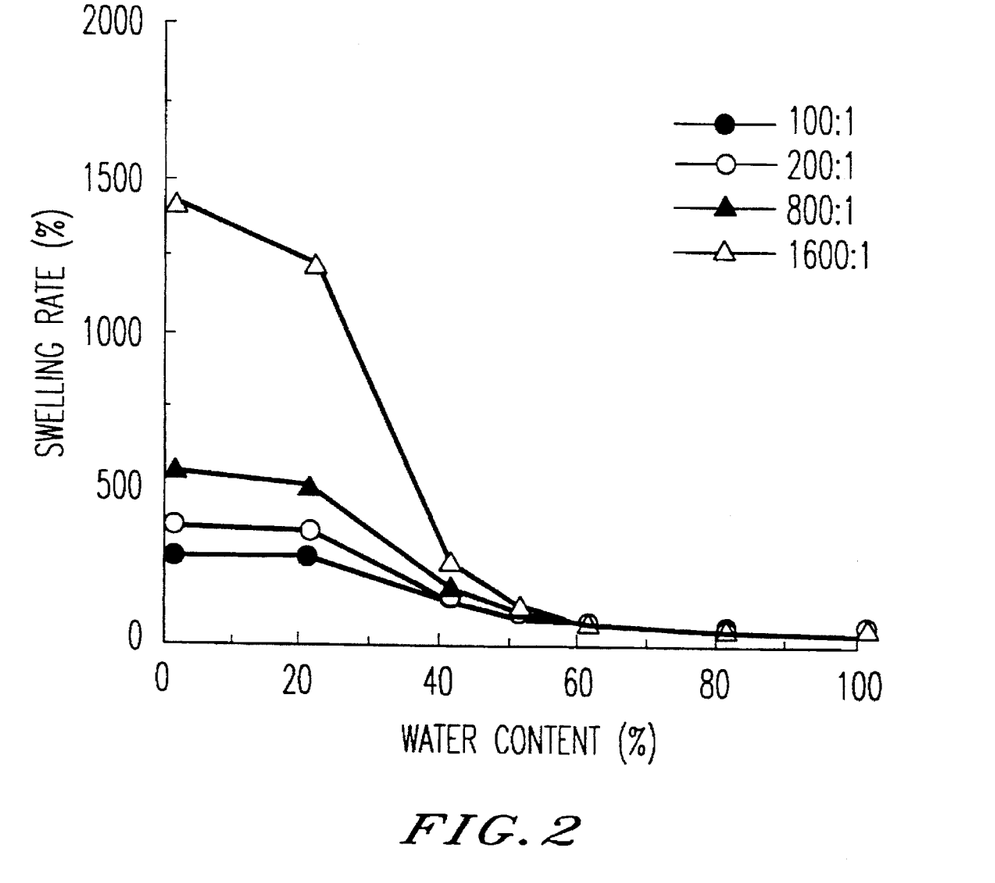
FIG. 2 diagrammatically illustrates a comparison in swelling rate among polymers with varied crosslink densities.

FIG. 2 shows a comparison in swelling rate among the plate-shaped polymers obtained in Example 4 at the varied crosslinking densities of EGDMA, a crosslink agent.

It was confirmed that the lower the crosslink density, the higher the swelling rate, particularly when the water content was low.

Figure 3:
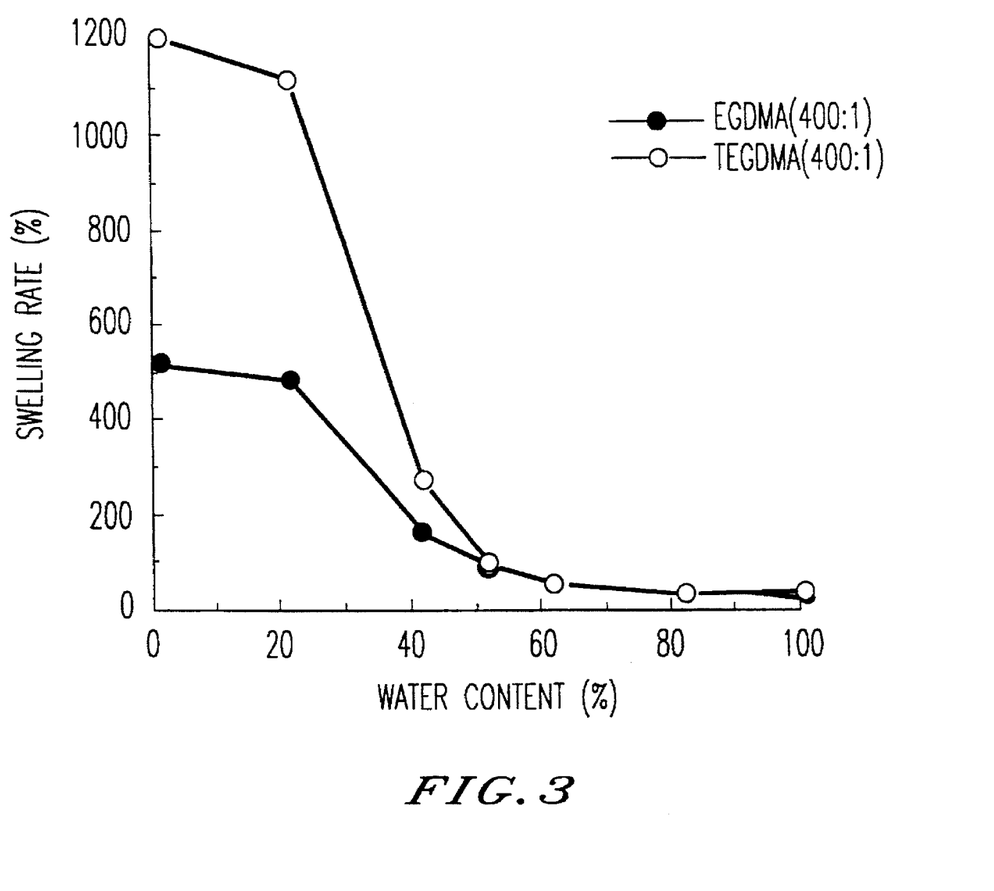
FIG. 3 diagrammatically illustrates a comparison in swelling rate among polymers obtained using crosslinking agents of varied chain lengths.

FIG. 3 shows a comparison in swelling rate between the two plate-shaped polymers obtained in Example 6 using the crosslinking agents of the different chain lengths. It was found that the plate-shaped polymer obtained using TEGDMA of the longer chain length had a higher swelling rate, particularly at a lower water content.

TEST 3

Figure 4:
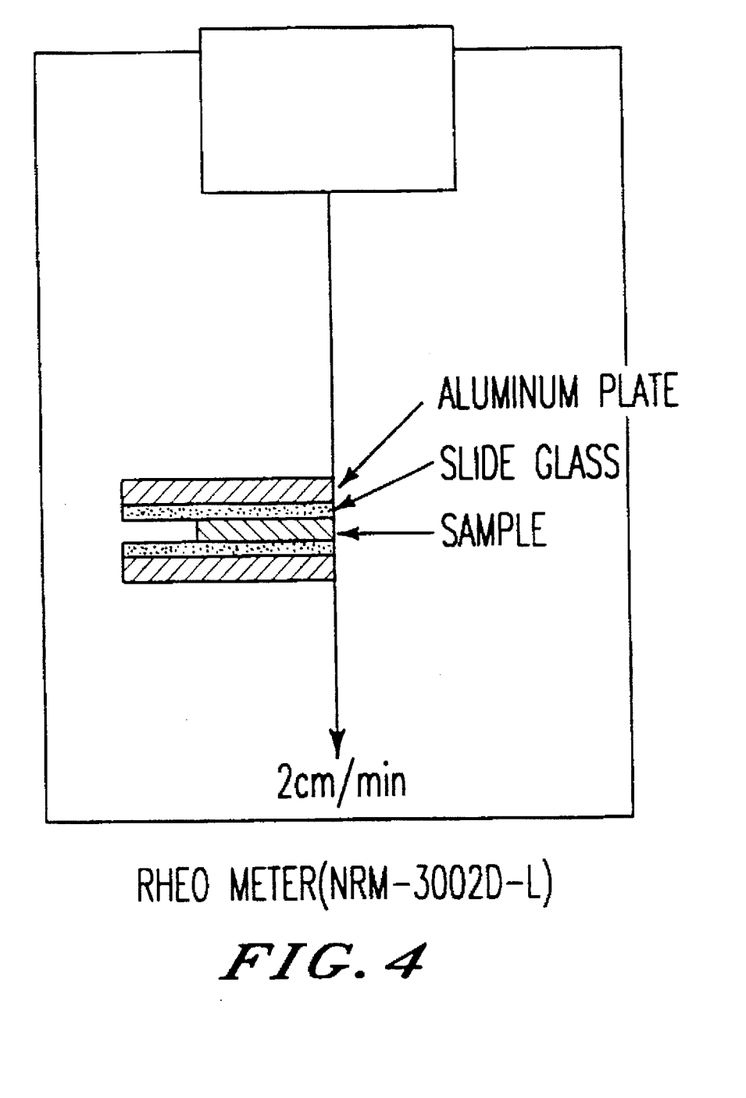
FIG. 4 depicts the construction of an apparatus used for the measurement of peel strength in Test 3.

The pads produced from the respective fine powdery polymers in Example 1 and the plate-shaped polymers obtained in Example 2 were each subjected to swelling until saturation in a mixed solvent of 50 parts by weight of PEG 400, 25 parts by weight of isopropyl alcohol and 25 parts by weight of water, followed by cutting into a sample piece of 1 cm×1 cm. Using an apparatus of the construction illustrated in FIG. 4, the sample piece was peeled off from glass at a fixed rate of 2 cm/min and the load at the time of the peeling was measured. In accordance with the above formula (2), the peel strength was calculated.

Figure 5:
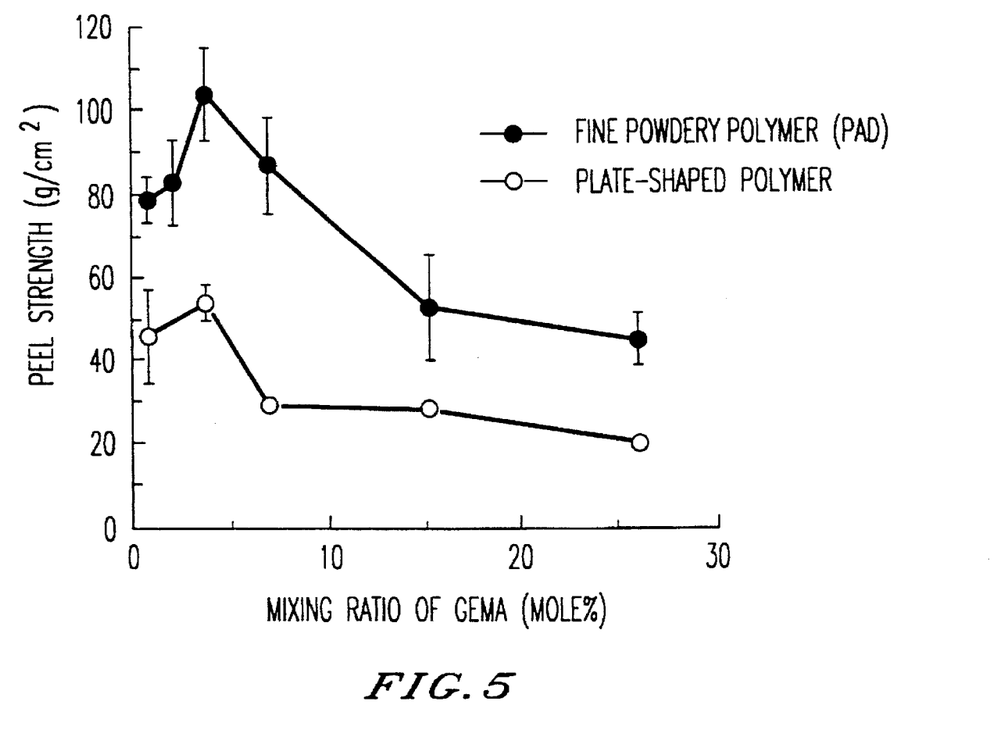
FIG. 5 diagrammatically illustrates a comparison in peel strength among polymers with varied proportions of GEMA.

FIG. 5 shows a comparison in peel strength between the pads of the fine powdery polymers and the plate polymers obtained at the varied proportions of GEMA in Example 1 and Example 2, respectively.

It was found that the pads had greater adhesion strength irrespective of the amount of GEMA and showed the maximum value at the GEMA amount of 3.3 mole % (at a GEMA:HEMA:BA molar ratio of 1:19:10).

Figure 6:
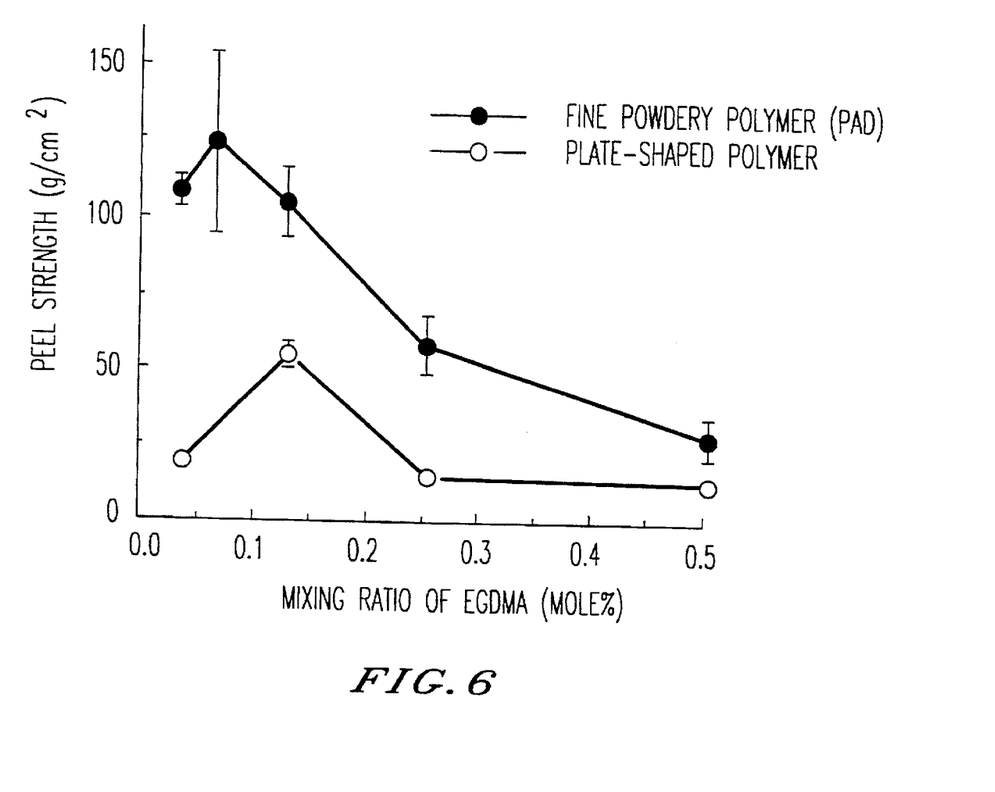
FIG. 6 diagrammatically illustrates a comparison in peel strength among polymers with varied crosslink densities.

FIG. 6 shows a comparison in peel strength between the pads, which had been produced from the respective fine powdery polymers obtained at varied crosslink densities by changing the proportion of EGDMA in Example 3, and the plate-shaped polymers obtained likewise in Example 4.

It was found that the lower the crosslink density, the higher the peel strength. When the amount of EGDMA was 0.125 mole % (at a crosslink density of 800:1) or smaller, no substantial change was observed. Furthermore, the pads showed greater adhesion strength.

Figure 7:
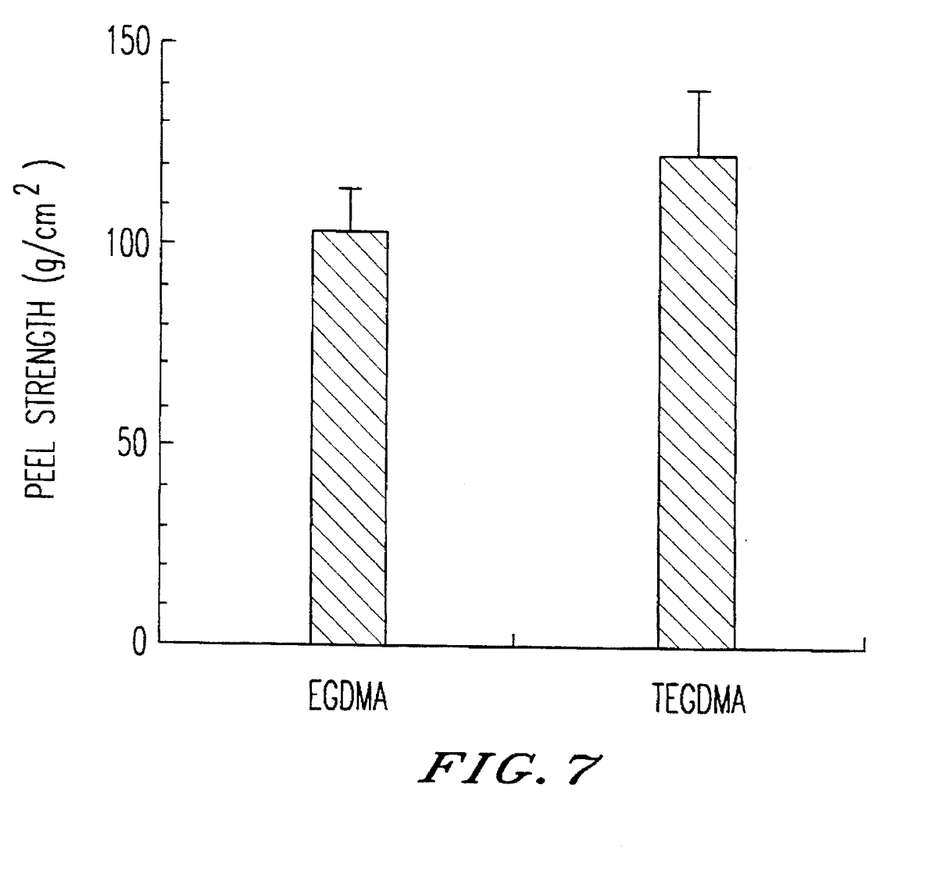
FIG. 7 diagrammatically illustrates a comparison in peel strength among polymers obtained using crosslinking agents of varied chain lengths.

FIG. 7 shows a comparison in peel strength between the pads obtained in Example 5. The pads were made from the powdery polymers for which the crosslinking agents of different chain lengths had been used, respectively.

It was found that the pad obtained using TEGDM had greater adhesion strength and a higher swelling rate.

EXAMPLE 7

A dermatologic medicine containing indomethacin therein was prepared in the form of a pad and after application of the pad, the blood level of indomethacin was measured along the passage of time.

(1) Preparation of pads:

An indomethacin solution having a composition shown in Table 1 was prepared.

TABLE 1

|  | (wt. %) |
|---|---|
| Indomethacin | 1.2 |
| Polyethylene glycol 400 | 50.0 |
| Isopropyl alcohol | 24.4 |
| Purified water | 24.4 |

To a 1:19:10 (by molar ratio) monomer mixture of GEMA, HEMA and BA, EGDMA was added at a molar ratio of 800:1. As in Example 1, a polymer was obtained in the form of fine powder.

The resulting fine powdery polymer (1 part by weight) and 5 parts by weight of the above indomethacin solution were mixed. Out of the resulting mixture, 4.9 g were weighed. It was placed between two silicone sheets with a 5-mm thick spacer interposed therebetween, followed by spreading into a 7 cm×7 cm pad.

(2) Testing method

After the abdominal skin of each of JW rabbits (average weight: 2.5 kg, male) was epilated, the pad was applied to a central part of the epilated skin. Upon elapsed times of 2, 4 and 6 hours after the application of the pad, 1 ml blood samples were collected from his heart, respectively, and the indomethacin concentrations in their plasma portions were measured by HPLC.

(3) Results

Figure 8:
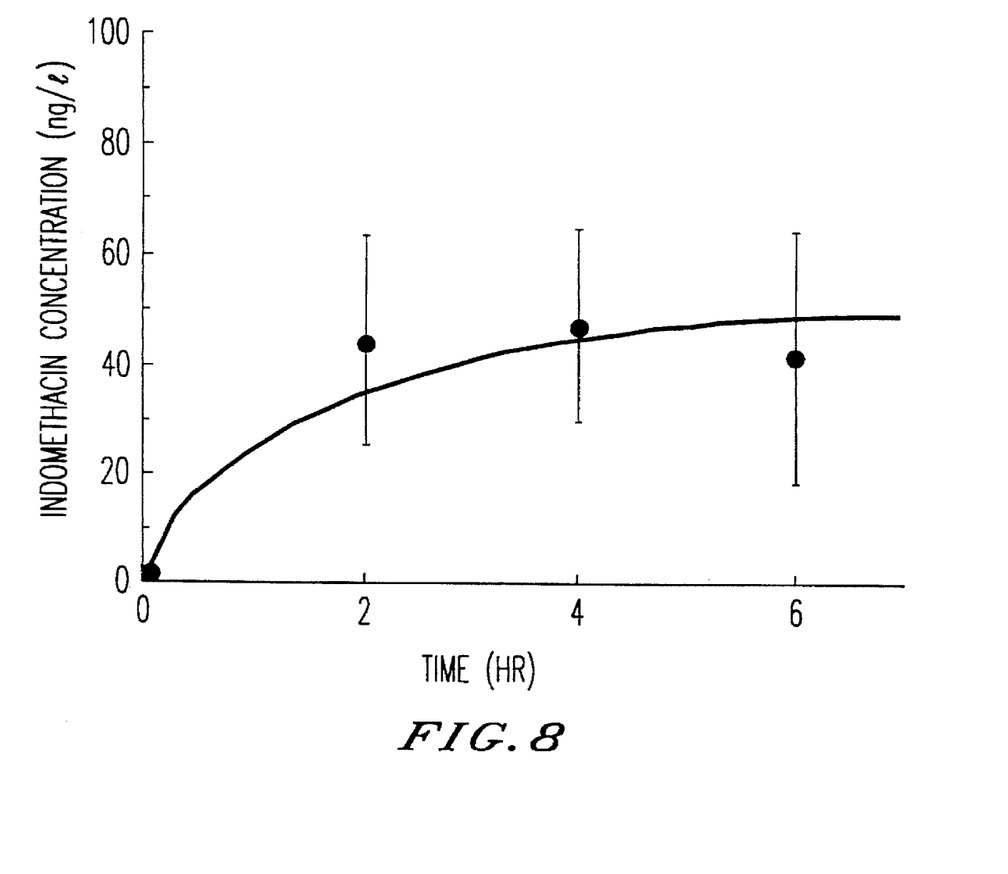
FIG. 8 diagrammatically shows time-dependent changes in the blood level of indomethacin in Example 7.

Time-dependent changes of the blood level of indomethacin are diagrammatically shown in FIG. 8.

From the results, it was confirmed that indomethacin was absorbed to a sufficient blood level in 2 hours and moreover, that blood level remained over an extended time. Good percutaneous absorption was therefore confirmed.

What is claimed is:

1. An adhesive base material comprising a polymer obtained by polymerizing a glucosyloxy alkyl (meth) acrylate, a hydroxyalkyl (meth)acrylate, an alkyl (meth) acrylate and a polyfunctional monomer, and wherein a molar ratio of the glucosyloxy alkyl (meth)acrylate, hydroxyalkyl (meth)acrylate and alkyl (meth)acrylate falls within a range of 0.1–10:10–40:5–20.

2. An adhesive base material according to claim 1, wherein a molar ratio of the polyfunctional monomer and the sum of the glucosyloxy alkyl (meth)acrylate, hydroxy alkyl(meth)acrylate and alkyl(meth)acrylate falls within a range of from 1:100 to 1:3200.

3. An adhesive base material according to claim 1 comprising a polymer obtained by polymerizing 2-glucosyloxyethyl (meth)acrylate, 2-hydroxyethyl (meth) acrylate, n-butyl (meth)acrylate and ethylene glycol di(meth)acrylate.

4. An adhesive base material according to any one of claims 1, 2 or 3, wherein the polymer has been impregnated with a mixed solvent of an alcohol and water.

5. An adhesive base material according to claim 4, wherein the polymer has been impregnated with a mixed solvent of a polyhydric alcohol, a monohydric alcohol and water.

6. An adhesive base material according to claim 5, wherein the polyhydric alcohol, a monohydric alcohol and water have been mixed at a weight ratio of 0.5–5:0.1–2:1.

7. An adhesive base material according to claim 4, wherein the polymer has been pulverized.

8. An adhesive base material according to claim 7, wherein the alcohol and water have been mixed at a weight ratio of from 1:1 to 1:10.

9. An adhesive base material according to claim 8, wherein the polymer impregnated and swelled with the solvent has a swelling rate of at least 300%.

10. An adhesive base material according to claim 9, wherein the polymer has peel strength of at least 80 g/cm$^2$ when measured relative to glass.

11. A dermatologic medicine comprising an adhesive base material according to claim 1 and a medicament.

12. A dermatologic medicine according to claim 11, wherein the medicament is any one of an antipyretic, antiphlogistic and analgesic agent, a steroidal anti-inflammatory agent, a vasodilator, an antihypertensive and antiarrhythmic agent, a hypotensive agent, an antitussive expectorant, an antineoplastic, a local anesthetic, a hormone preparation, an antiasthmatic and antiallergic agent, an antihistaminic, an anticoagulant, an antispasmodic, a cerebral circulation and metabolism improver, an antidepressant and antianxiety agent, a vitamin D preparation, a hypoglycemic agent, an antiulcer agent, a hypnotic and an antibiotic.

* * * * *